US012709597B2

(12) United States Patent
Almirante

(10) Patent No.: US 12,709,597 B2
(45) **Date of Patent: *Aug. 18, 2026**

(54) PROCESS FOR THE PREPARATION OF A NITRIC OXIDE DONATING PROSTAGLANDIN ANALOGUE

(71) Applicant: NICOX S.A., Sophia Antipolis-Valbonne (FR)

(72) Inventor: Nicoletta Almirante, Milan (IT)

(73) Assignee: NICOX S.A., Sophia Antipolis Valbonne (FR)

( * ) Notice: Subject to any disclaimer, the term of this patent is extended or adjusted under 35 U.S.C. 154(b) by 1060 days.

This patent is subject to a terminal disclaimer.

(21) Appl. No.: 17/631,559

(22) PCT Filed: Aug. 3, 2020

(86) PCT No.: PCT/EP2020/071766

§ 371 (c)(1),
(2) Date: Jan. 31, 2022

(87) PCT Pub. No.: WO2021/023693

PCT Pub. Date: Feb. 11, 2021

(65) Prior Publication Data

US 2022/0274924 A1 Sep. 1, 2022

(30) Foreign Application Priority Data

Aug. 5, 2019 (EP) .................................... 19189993

(51) Int. Cl.
*C07C 405/00* (2006.01)

(52) U.S. Cl.
CPC .... *C07C 405/0041* (2013.01); *C07C 2601/08* (2017.05)

(58) Field of Classification Search
CPC .......... C07C 405/0041; C07C 2601/08; C07C 405/00; C07C 51/412; C07C 201/00; Y02P 20/55; C07F 5/025; C07B 2200/07; C07B 2200/09
See application file for complete search history.

(56) References Cited

U.S. PATENT DOCUMENTS

| | | | | |
|---|---|---|---|---|
| 10,988,438 B2 * | 4/2021 | Almirante | ............. | C07C 291/02 |
| 2024/0018096 A1 * | 1/2024 | Kovács | ................... | A61P 27/02 |
| 2024/0158345 A1 * | 5/2024 | Almirante | ......... | C07C 405/0041 |

FOREIGN PATENT DOCUMENTS

| | | | |
|---|---|---|---|
| EP | 3530649 A1 | 8/2019 | |
| JP | 2015-227317 A | 12/2015 | |
| WO | WO-2009136281 A1 * | 11/2009 | ........... C07C 405/00 |

OTHER PUBLICATIONS

ISA/EP, International Search Report and Written Opinion mailed Oct. 22, 2020 issued in PCT Application No. PCT/EP2020/071766.
Office Action received for Japanese Patent Application No. 2022-506896, mailed on Jul. 23, 2024, 4 pages (2 pages of English Translation and 2 pages of Original Document).

* cited by examiner

*Primary Examiner* — James H Alstrum-Acevedo
*Assistant Examiner* — Chantal Adlam
(74) *Attorney, Agent, or Firm* — ArentFox Schiff LLP

(57) ABSTRACT

The present invention relates to a process for preparing the hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxy-cyclopentyl]-1-(2-phenylethyl)-2-propen-1-yl ester of formula (I).

(I)

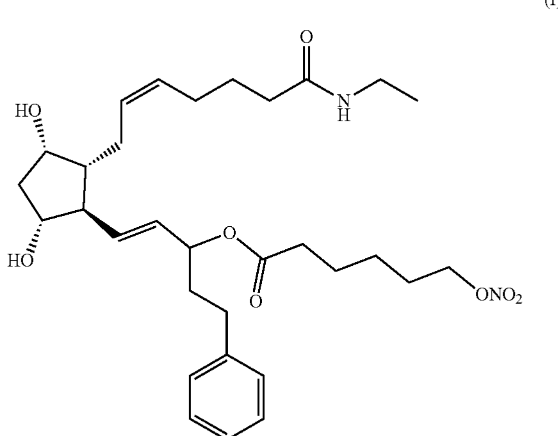

In accordance with the present invention, the compound (I) can be efficiently prepared with high purity by coupling bimatoprost in a boronate protected form with 6-(nitrooxy) hexanoyl chloride having an high chemical purity and removing the boronate protecting group.
The high chemical pure 6-(nitrooxy)hexanoyl chloride is prepared from 6-(nitrooxy)hexanoic acid having a high chemical purity. The invention also relates to a process for the preparation and purification of 6-(nitrooxy) hexanoic acid.

16 Claims, No Drawings

PROCESS FOR THE PREPARATION OF A NITRIC OXIDE DONATING PROSTAGLANDIN ANALOGUE

CROSS-REFERENCE TO RELATED APPLICATIONS

This application is a 35 U.S.C. § 371 National Phase of PCT Application No. PCT/EP2020/071766, filed Aug. 3, 2020, which claims priority to European Application No. 19189993.9, filed Aug. 5, 2019, the disclosures of which are hereby incorporated by reference herein.

FIELD OF THE INVENTION

The present invention relates to an improved process suitable for large scale preparation of hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester of formula (I) which allows to obtain said product having a high chemical purity. The present invention also describes the preparation of highly pure 6-(nitrooxy)hexanoic acid (VIIa) that is a key intermediate of the synthesis.

BACKGROUND OF THE INVENTION

Hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester of formula (I)

(I)

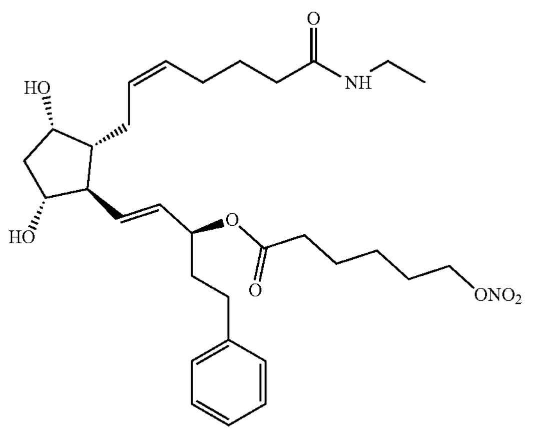

is a prostaglandin analogue that has proved effective as IOP-lowering agent (Impagnatiello F, Toris C B, Batugo M, Prasanna G, Borghi V, Bastia E, Ongini E, Krauss A H P; Invest Ophthalmol Vis Sci. 2015; 56:6558-64).

A process for preparing compound of formula (I) is disclosed in WO 2009/136281.

WO 2009/136281 specifically discloses the synthesis of compound (I) and in general the preparation of 15-alkyl nitrate esters of bimatoprost.

WO 2009/136281 discloses the synthesis of compound of formula (I) (Example B-1) by reacting bimatoprost in a boronate protected form (compound (II)) with 6-bromohexanoyl chloride to give the 15-(6-bromohexanoyl) ester of bimatoprost in a boronate protected form (compound (XI)) that is converted into the nitrate derivative by silver nitrate in acetonitrile and deprotected/purified under reverse phase chromatography yielding compound of formula (I).

(II)

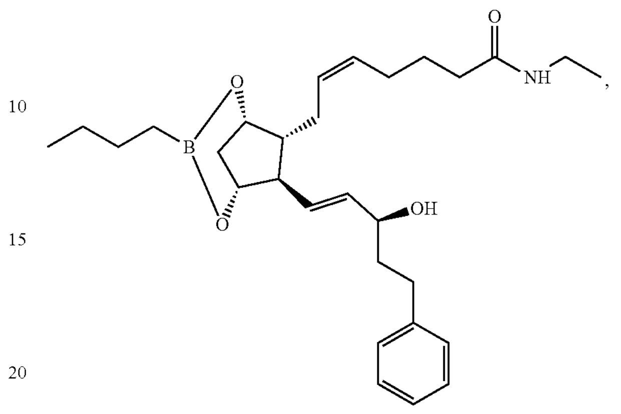

(XI)

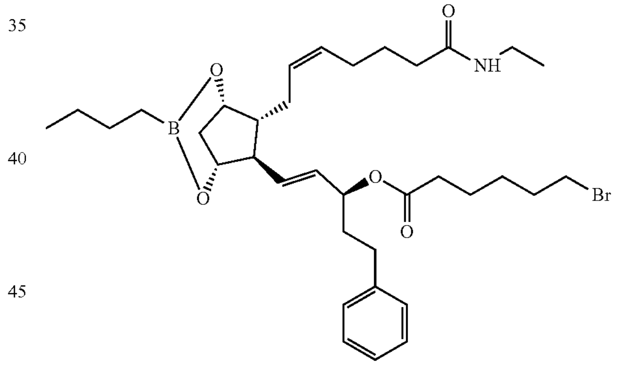

The main disadvantages of the above synthesis are the use in the esterification reaction of more than an equimolar amount of 6-bromohexanoyl chloride, which presents a structural alert for potential mutagenicity, and, in the last step, the use of silver nitrate that generates a large amount of silver salts in wastewater. Another main disadvantage of this process is the formation of impurities and by products such as 15-(6-bromohexanoyl) ester of bimatoprost (compound (IX)) and 15-(6-chlorohexanoyl) ester of bimatoprost (compound (X)) which are difficult to be removed even after multiple purifications, as they have similar polarity in chromatography, similar lipophilicity and/or solubility as those of compound (I). Moreover compound (X) is predicted as positive for bacterial in vitro mutagenicity. Removal of these impurities requires repeated purifications, which further reduces the yield and increases the cost of manufacturing on a commercial scale.

(IX)

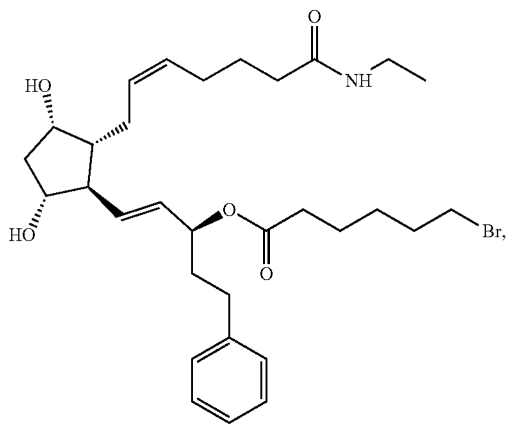

(X)

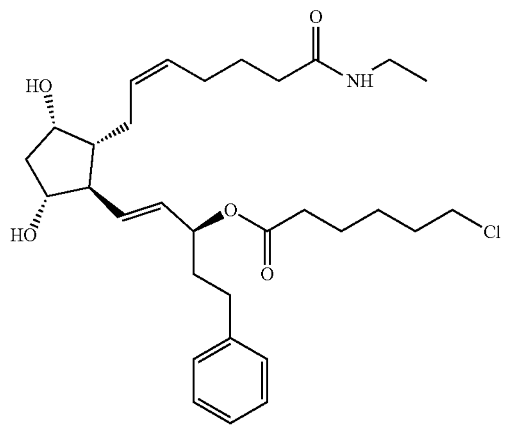

According to the procedure disclosed in WO 2009/136281, 15-(6-bromohexanoyl) ester of bimatoprost (compound (IX)) is an impurity deriving from uncompleted reaction of compound (XI) with silver nitrate, after removal of the boronate protection. 15-(6-Chlorohexanoyl) ester of bimatoprost (compound (X)) is a by-product formed by halogen exchange reaction between the bromine atom of 15-(6-bromohexanoyl) ester of bimatoprost in a boronate protected form (compound (XI)) and the free chlorine anion of 4-dimethylaminopyridine hydrochloride formed during the esterification step. The 15-(6-chlorohexanoyl) ester of bimatoprost in a boronate protected form (XIa) (Scheme 3) does not react with silver nitrate and, after removal of the protective group, yields compound (X).

WO 2009/136281 also discloses an alternative process for the preparation of 15-acylalkynitrate bimatoprost derivatives (Examples N-1 and O-1). The synthesis comprises reacting bimatoprost in a boronate protected form (compound of formula (II)) with a nitrate-alkyl carboxylic acid chloride in the presence of 4-dimethylaminopyridine (DMAP) supported on resin (PS-DMAP), followed by removal of the boronate protecting group and purification using silica gel chromatography.

The above process avoids the use of 6-bromohexanoyl chloride and the removal of the silver salts from the final product. However, this method presents another main disadvantage that is the use of 4-dimethylaminopyridine supported on resin which makes the process unsuitable for commercial scale-up and expensive. Furthermore, nitrate-alkyl carboxylic acid chloride is added in two successive steps and in high excess with respect to compound of formula (II), indeed the alkyl carboxylic acid chloride is added in an amount from about 2 to 4 equivalents.

WO 2009/136281 also discloses another process (Examples Q1) for the preparation of 15-acylalkynitrate bimatoprost derivatives. In this process the compounds were obtained by esterification of bimatoprost in a boronate protected form (II) with an excess of nitrate-alkyl-(p-nitrophenyl)-carboxylate in the presence of 4-dimethylaminopyridine.

The removal of the unreacted nitrate-alkyl-(p-nitrophenyl)-carboxylate and of the by-product p-nitrophenol, formed in equimolar amounts to compound of formula (I), using chromatography methods are the main disadvantages of this process.

WO 2016/155906 discloses 15-nitrooxyderivatives of fluprostenol and it reports the synthesis of the 15-nitrooxyhexyl ester of fluprostenol isopropyl ester. The compound was prepared by reacting fluprostenol isopropyl ester in a boronate protected form with (4-nitrophenyl)-6-nitrooxyhexanoate in the presence of 4-dimethylaminopyridine excess.

As reported above the removal of the unreacted nitrate-alkyl-(p-nitrophenyl)-carboxylate and, especially, the removal of the p-nitrophenol by-product by chromatography methods are the main disadvantages of this process.

EP 3 530 649 A1, which was filed before and published after the relevant date of the present invention, discloses a process for the preparation of hexanoic acid, 6-(nitrooxy), (1S,2E)-3-[(1R,2R,3S,5R)-2-[(2Z)-7-(ethylamino)-7-oxo-2-hepten-1-yl]-3,5-dihydroxy cyclopentyl]-1-(2-phenylethyl)-2-propen-1-yl ester (compound (I)). The compound (I) is prepared by coupling bimatoprost in a boronate protected form with 6-(nitrooxy)hexanoyl chloride and removing the boronate protecting group. The 6-(nitrooxy)hexanoyl chloride intermediate is prepared from the 6-(nitrooxy)hexanoic acid that is prepared by a ring-opening reaction of 2-caprolactone and subsequent nitration of the 6-hydroxyhexanoic acid potassium salt with a mixture of $HNO_3$ and $H_2SO_4$ in dichloromethane. The 6-(nitrooxy)hexanoic acid is used for the preparation of the correspondent acyl chloride without purification.

In the past few years, various regulatory authorities have been emphasizing on the purity requirements and the identification of impurities in the Active Pharmaceutical Ingredients (API). Currently, any impurity is considered as an organic material, besides the drug substance, that may influence the efficacy and safety of the pharmaceutical products. Therefore, the identification of each impurity and the quantification of the impurities, especially those bearing structural alert for mutagenicity, have become mandatory regulatory requirements. In addition, since the products are intended for pharmaceutical use, the range of industrially acceptable reagents, solvents, catalysts, etc. which can be used in the synthesis of the active ingredient is limited to those having pharmaceutical industry acceptability.

The compound of formula (I) is an oil and its purification in large scale quantities is difficult as it cannot be crystallized, therefore the presence of impurities is a critical issue for a large scale production. Since the main sources of impurities are the intermediates and the by-products of the synthesis, the purity of the intermediates and the control of the reactions conditions are important requirements for obtaining the final product having a pharmaceutical acceptable purity.

To summarize, the prior art processes for the preparation of compound of formula (I) have some disadvantages; e.g. the use of 6-bromohexanoyl chloride and the reaction conditions lead to the formation of the by-product 15-(6-chlorohexanoyl) ester of bimatoprost (compound (X)) that is predicted as positive for bacterial in vitro mutagenicity, based on both a statistical-based method and on an expert rule-based method, as required by Regulatory agencies; the use of silver nitrate for the preparation of the intermediate nitrate-alkyl carboxylic acid chloride or for the nitration of the 15-(6-bromohexanoyl) ester of bimatoprost in a boronate protected form (compound (XI)) lead to the management of a large amount of silver nitrate wastewater, moreover metal content in the Active Pharmaceutical Ingredients must satisfy specific acceptance criterion.

Thus there is a need to develop an industrially viable process providing high-purity hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester (compound (I)) in good yield.

Compound (I) can be efficiently prepared by coupling bimatoprost in a boronate protected form (compound (II)) with the 6-(nitrooxy)hexanoyl chloride that is prepared by ring-opening reaction of caprolactone with an alkali metal hydroxide solution followed by nitration of the 6-hydroxyhexanoic acid alkali metal salt using a mixture of $HNO_3$ and $H_2SO_4$, leading to the 6-(nitrooxy)hexanoic acid that is converted to the 6-(nitrooxy)hexanoyl chloride; the 6-(nitrooxy)hexanoic acid and 6-(nitrooxy)hexanoyl chloride are used without further purification. However experiments conducted by the Applicant showed that compound (I) prepared using this process contains a “dimer impurity” 6-{[6-(nitrooxy)hexanoyl]oxy}hexanoic acid ester of bimatoprost (compound (XII)

(XII)

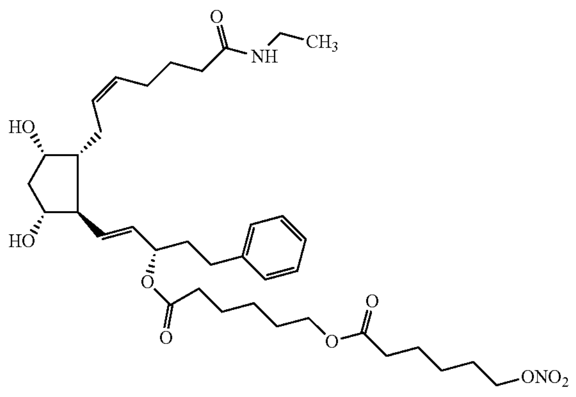

Compound (I) and compound (XII) have similar polarity in chromatography, therefore removing compound (XII) requires repeated purifications that reduce the yield of the process.

Compound (XII) is formed when 6-{[6-(nitrooxy) hexanoyl]oxy}hexanoyl chloride (compound (IVb)) reacts with compound (II) during the coupling step.

It is found that the acidic reaction condition of the nitration of the 6-hydroxyhexanoic acid alkali salt, which is performed using a mixture of $HNO_3$ and $H_2SO_4$, leads to the formation of the 6-[6-hydroxyhexanoyl]oxy}hexanoic acid impurity that, in the presence of $HNO_3$, is transformed into the nitrate derivative 6-{[6-(nitrooxy)hexanoyl] oxy}hexanoic acid (compound (VIIb))

(VIIb)

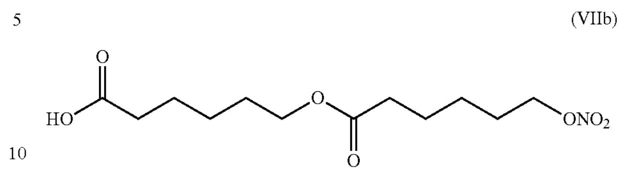

Therefore reacting the crude product of the nitration reaction without any purification, with a chlorinating agent leads to the formation of 6-(nitrooxy)hexanoyl chloride (IVa) and the 6-[6-hydroxyhexanoyl]oxy}hexanoyl chloride (IVb):

(IVa)

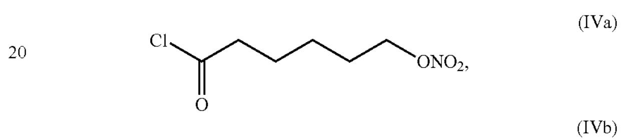

(IVb)

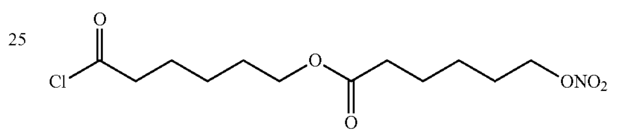

It has been found that the key factor to obtain compound (I) in high yield and high purity is the use of high pure 6-(nitrooxy)hexanoic acid intermediate (VIIa)

(VIIa)

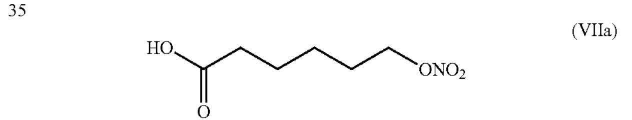

that can be obtained by purifying the crude product of the nitration reaction using reverse phase chromatography.

The present invention provides a process suitable for large scale production that allows obtaining hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester (compound (I)) in good yield, containing an amount of the predicted genotoxic impurity 15-(6-chlorohexanoyl) ester of bimatoprost (X) below the safety level and an amount of the “dimer impurity” 6-{[6-(nitrooxy)hexanoyl]oxy}hexanoic acid ester of bimatoprost (compound (XII)) less than 0.1% w/w.

The “safety level amount” is calculated according to the Threshold of Toxicological Concern (TTC) acceptable intake of 1.5 μg/day for chronic treatment.

Furthermore, the present invention relates to a process for the preparation of highly pure 6-(nitrooxy)hexanoic acid intermediate of formula (VIIa).

(VIIa)

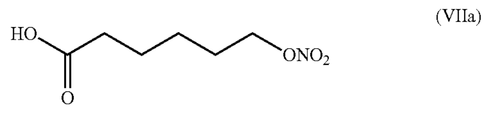

DESCRIPTION OF THE INVENTION

Object of the present invention is a process for the preparation of hexanoic acid, 6-(nitrooxy)-, (1S,2E)-3-[(1R, 2R,3S,5R)-2-[(2Z)-7-(ethylamino)-7-oxo-2-hepten-1-yl]-3, 5-dihydroxycyclopentyl]-1-(2-phenylethyl)-2-propen-1-yl ester of formula (I):

(I)

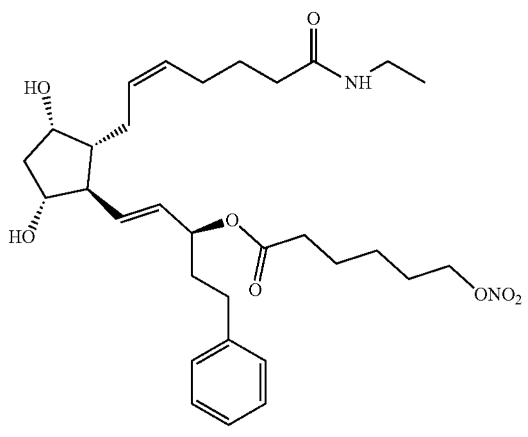

said process comprising the following steps:

1) reacting compound (II):

(II)

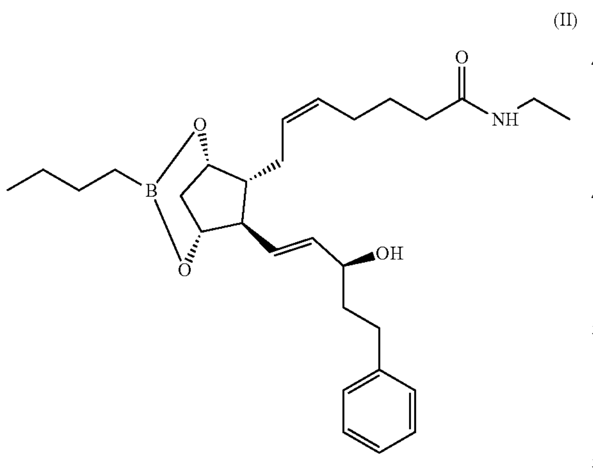

with 6-(nitrooxy)hexanoyl chloride (IVa)

(IVa)

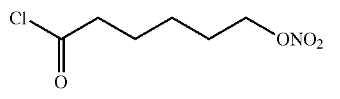

in the presence of 4-dimethylaminopyridine in free form, to obtain the compound (III)

(III)

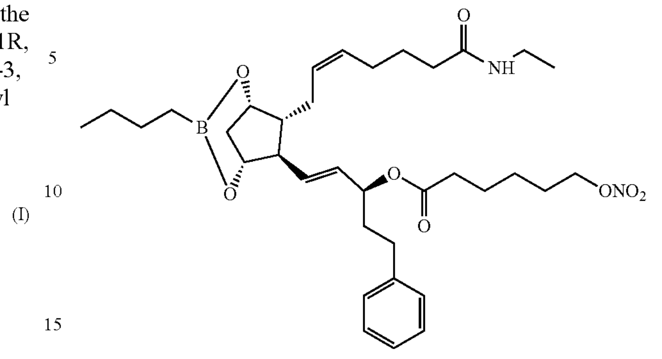

2) removing the boronate protective group of the compound (III) to obtain compound of formula (I);

3) purification of the compound (I);

wherein said process is characterized in that the 6-(nitrooxy) hexanoyl chloride (compound (IVa) is prepared by a process comprising the following steps:

4) reacting the 2-caprolactone (V):

(V)

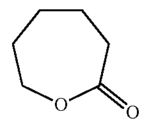

with an inorganic base selected from KOH, NaOH and LiOH to obtain 6-hydroxyhexanoic acid salt of formula (VI):

(VI)

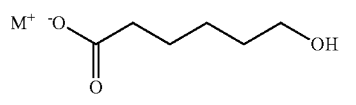

wherein M is K, Na or Li.

5) nitrating a compound of formula (VI) with a mixture of $HNO_3$ and $H_2SO_4$ to obtain the 6-(nitrooxy)hexanoic acid (VIIa)

(VIIa)

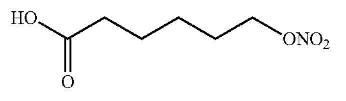

The obtained product (VIIa) may contain amount of the by-product 6-{[6-(nitrooxy)hexanoyl]oxy}hexanoic acid (VIIb) of 1% w/w (VIIb)

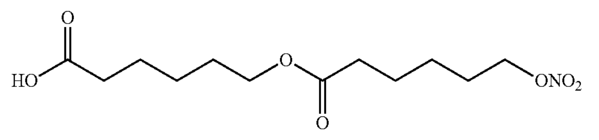

6) purifying the nitration mixture by reverse phase chromatography using formic acid in water ($H_2O$+HCOOH) and acetonitrile as eluent; to obtain pure 6-(nitrooxy)hexanoic acid of formula (VIIa) having a content of compound (VIIb) below the HPLC detection limits (<0.05%)

7) reacting the pure 6-(nitrooxy)hexanoic acid (VIIa) with a chlorinating agent to obtain 6-(nitrooxy)hexanoyl chloride (IVa).

Preferably, the 6-(nitrooxy)hexanoyl chloride obtained in step 7) is directly reacted with compound of formula (II) in step 1) without further purification.

The step 1) is carried out at a temperature ranging from 0° C. to room temperature and it is preferably carried out in an aprotic organic solvent, preferably selected from methyltertbutyl ether, N,N-dimethylformamide or dichloromethane. Most preferably, the organic solvent is methyltertbutyl ether. 4-Dimethylaminopyridine (DMAP) in free form means that DMAP is not bound to a resin.

The molar ratio of compound (II) to 6-(nitrooxy)hexanoyl chloride (IVa) preferably ranges from 1:1.4 to 1:1.6.

The molar ratio of compound (II) to 4-dimethylaminopyridine preferably ranges from 1:2.0 to 1:2.4.

In step 2), the removal of the boronate protecting group is preferably carried out using methanol at a temperature from 17° C. to 24° C.

In step 4) the used inorganic base is preferably potassium hydroxide.

Step 4) is preferably carried out in a solvent selected from methanol, ethanol or isopropanol, most preferably methanol.

Steps 5) and 7) are carried out in dichloromethane.

In step 6) the concentration of formic acid in water ($H_2O$+HCOOH) is 0.1%. Preferably, pure 6-(nitrooxy)hexanoic acid of formula (VIIa) is obtained by extracting the fractions containing the compound (VIIa) with $CH_2Cl_2$, drying with MgSO4 and evaporating the solvent.

The preferred chlorinating agent used in step 7) is oxalyl chloride.

Compound (II) is obtained by reacting bimatoprost with butylboronic acid. Preferably the reaction is carried out in methyltertbutyl ether as solvent.

A further object of the present invention is a process for the preparation of compound (VIIa) is described below and depicted in Schemes 1 (the reference numbers of the steps reported in the scheme correspond to those reported above), said process comprising:

step 4) reacting the 2-caprolactone (V) with potassium hydroxide in methanol to obtain 6-hydroxyhexanoic acid potassium salt (compound of formula (VI) wherein M is potassium);

step 5) reacting 6-hydroxyhexanoic acid potassium salt with a mixture of $HNO_3$ and $H_2SO_4$ in dichloromethane to obtain the crude 6-(nitrooxy)hexanoic acid (VIIa) that contains the by-product 6-{[6-(nitrooxy)hexanoyl]oxy}hexanoic acid (VIIb)), preferably at a temperature from about 5° C. to 10° C., preferably 10° C.;

step 6) purifying the crude mixture containing 6-(nitrooxy)hexanoic acid (VIIa) and 6-{[6-(nitrooxy)hexanoyl]oxy}hexanoic acid (VIIb) with reverse phase chromatography, such as for example C18, 25µ—Standard Type Flash Cartridge) preferably using $H_2O$+HCOOH 0.1%/acetonitrile from 90:10 to 75:25 as eluent and extracting the fractions containing compound (VIIa) with $CH_2Cl_2$ to obtain pure 6-(nitrooxy)hexanoic acid (VIIa) containing an amount of the by-product 6-{[6-(nitrooxy)hexanoyl]oxy}hexanoic acid (VIIb) below the HPLC detection limits (<0.05%).

The pure compound (VIIa) obtained in the above step 6) can be used in step 7) by reacting the pure 6-(nitrooxy)hexanoic acid with oxalyl chloride to obtain 6-(nitrooxy)hexanoyl chloride (IVa) that is used without further purification in the process for obtaining the compound of formula (I) as described above.

A preferred process for preparing the compound of formula (I) is depicted in Scheme 2, said preferred process comprises the steps:

step 1a) reacting bimatoprost with butyl boronic acid (1.1-1.8 eq) in methyltertbutyl ether (MTBE) at temperature about 40° C., then removing water by azeotropic distillation to obtain bimatoprost boronate (II);

step 1) reacting bimatoprost boronate (II) with 6-(nitrooxy)hexanoyl chloride (IVa), (1.4-1.6 equivalent) in methyltertbutyl ether in the presence of 4-dimethylaminopyridine (2.0-2.4 equivalent) at a temperature ranging from 0° C. to about room temperature, to obtain (1S,2E)-3-{(6R,7R)-3-butyl-7[(2Z)-7-(ethylamino)-7-oxohept-2-en-1-yl]-2,4-dioxa-3-borabicyclo[3.2.1]oct-6-yl}-1-(2-phenylethyl)-prop-2-en-1-yl 6-(nitrooxy)hexanoate (III);

step 2) reacting (1S,2E)-3-{(6R,7R)-3-butyl-7[(2Z)-7-(ethylamino)-7-oxohept-2-en-1-yl]-2,4-dioxa-3-borabicyclo[3.2.1]oct-6-yl}-1-(2-phenylethyl)-prop-2-en-1-yl 6-(nitrooxy)hexanoate (III) with methanol at room temperature to remove the protective group and to obtain the crude hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester (I); the HPLC quantitative analysis of the crude reaction mixture detects a content of compound (I) of about 70%, an amount of 15-(6-chlorohexanoyl) ester of bimatoprost (Compound (X)) of about 0.12% and an amount of dimeric impurity 6-{[6-(nitrooxy)hexanoyl]oxy}hexanoic acid ester of bimatoprost (compound (XII)) below the HPLC detection limit of 0.05% (see Table 1).

step 3) purifying the crude reaction mixture of Step 2 by chromatography to obtain hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester (I) having a chemical purity above 98%, an amount of 15-(6-chlorohexanoyl) ester of bimatoprost (compound (X)) about 0.12% and an amount of the dimeric impurity 6-{[6-(nitrooxy)hexanoyl]oxy}hexanoic acid ester of bimatoprost (compound (XII)) below the HPLC detection limit of 0.05%.

SCHEME 1
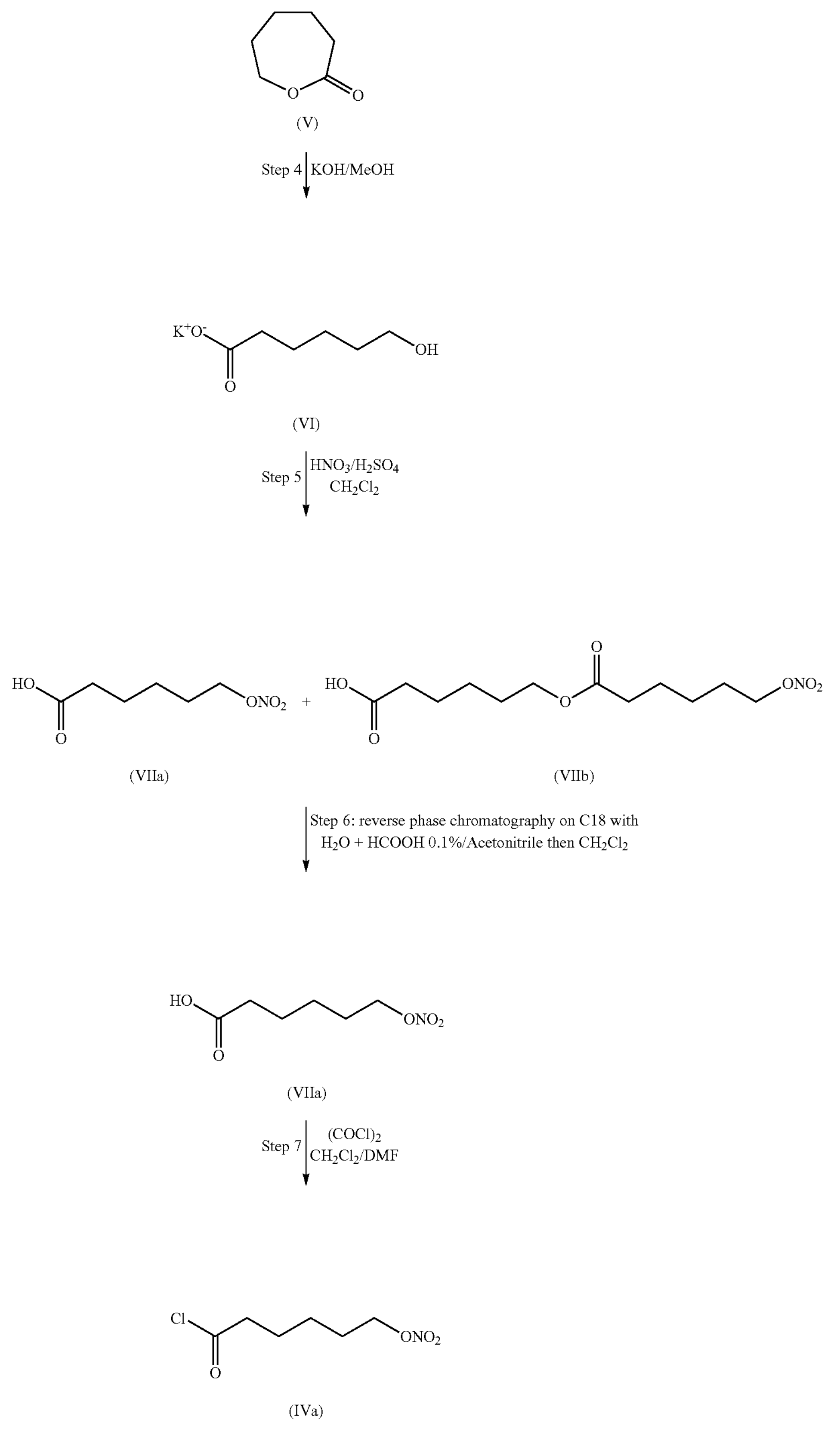

SCHEME 2
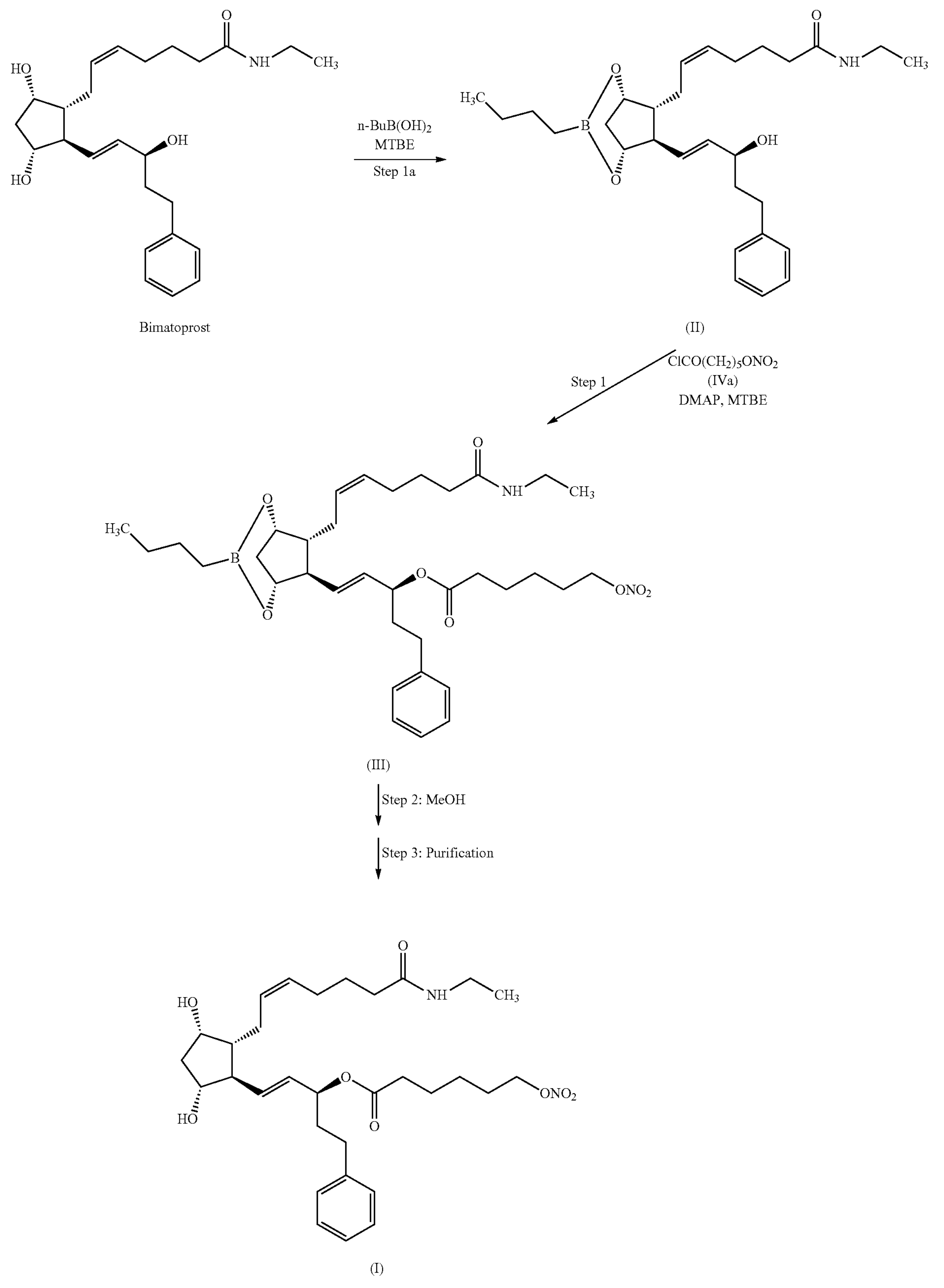
Bimatoprost
(II)
(III)
(I)

The experimental procedures of the steps of the process of the invention are described in detail below.

A further object of the present invention is hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester of formula (I) having a chemical purity above 98% and containing an amount of 15-(6-chlorohexanoyl) ester of bimatoprost (compound (X)) of about 0.12%

(X)

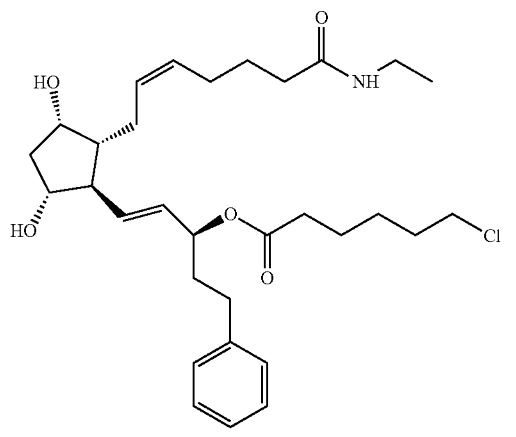

and an amount of 6-{[6-(nitrooxy)hexanoyl]oxy}hexanoic acid ester of bimatoprost (compound (XII)) below 0.05%

(XII)

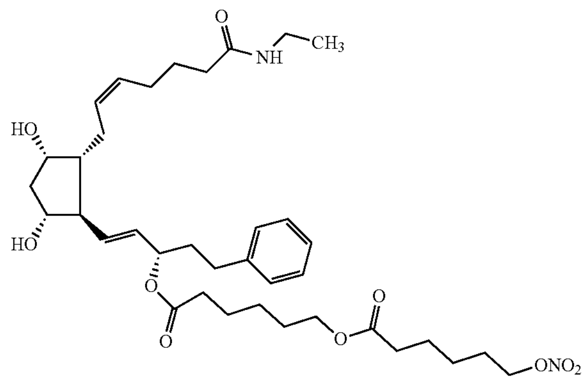

Another object of the invention is a pharmaceutical formulation containing hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester of formula (I) and at least a pharmaceutically acceptable excipient, wherein hexanoic acid, 6-(nitrooxy)-, (1 S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester has a chemical purity above 98%, and contains an amount of 15-(6-chlorohexanoyl) ester of bimatoprost (compound (X)) about 0.12% and an amount of the dimeric impurity 6-{[6-(nitrooxy)hexanoyl]oxy}hexanoic acid ester of bimatoprost (compound (XII)) below 0.05%.

General Synthesis

Preparation of 6-(Nitrooxy)hexanoyl chloride (IVa)

All steps are carried out under nitrogen atmosphere.

Preparation of 6-hydroxyhexanoic acid potassium salt (Compound (VI))

A solution of potassium hydroxide (1 equivalent) in methanol is dropwise added to a solution of 2-caprolactone (1 equivalent) in methanol; the mixture is cooled at about 5° C. to 20° C. and stirred for about 5 hours at 15° C. to 20° C. after the addition is over; the solvent is removed (temperature is equal to or below 40° C.), the crude product is slurred in methyltertbutyl ether, 6-hydroxyhexanoic acid potassium salt is filtered, washed with methyltertbutyl ether and dried. 6-hydroxyhexanoic acid potassium salt (VI) is obtained with a 95% yield and a purity of 98.5% ($^1$H-NMR and HCl assay).

Preparation of 6-(nitrooxy)hexanoic acid (Compound (VIIa))

6-hydroxyhexanoic acid potassium salt (VI) (1 equivalent) is portion-wise added to a mixture of $HNO_3$ (4.6 equivalent) and $H_2SO_4$ (3.1 equivalent) in dichloromethane cooled at 0° C. to 5° C. under nitrogen in about 30 min while keeping the temperature below 10° C.; the resulting mixture is stirred for 2-3 hours at 0° C. to 10° C. monitoring the end of the reaction by $^1$H-NMR analysis; the mixture is cooled at a temperature from 0° C. to 5° C. and dropwise added with a saturated sodium chloride aqueous solution in around 20 min. The reaction mixture is maintained at a temperature below 10° C.; the organic layer is dried over anhydrous sodium sulfate, the solvent is removed to give 6-(nitrooxy) hexanoic acid (VIIa) in 86-88% yield and 96.2% HPLC purity. The main impurity is the dimeric compound 6-{[6-(nitrooxy)hexanoyl]oxy}hexanoic acid (compound (VIIb)) (about 1%).

(VIIb)

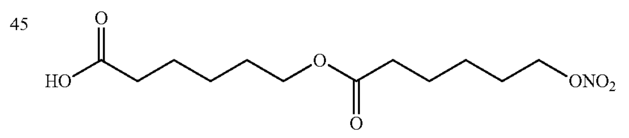

The crude 6-(nitrooxy)hexanoic acid (compound (VIIa)) (1 equivalent) is loaded on a Purezza®-SpheraPlus Flash Cartridges—C18, 25μ—Standard Type Flash Cartridge, 48 g, and eluted with $H_2O$+HCOOH 0.1%/Acetonitrile from 90:10 to 75:25. The fractions containing compound (VIIa) are collected and extracted with $CH_2Cl_2$ and dried, the solvent is evaporated to give pure 6-(nitrooxy)hexanoic acid in 80-90% yield. HPLC purity of compound (VIIa) is 99% and the content of compound (VIIb) is less than 0.05%.

Preparation of 6-(nitrooxy)hexanoyl chloride (Compound (IVa))

N,N-dimethylformamide and oxalyl chloride are dropwise added to a solution of 6-(nitrooxy)hexanoic acid in dichloromethane, keeping the temperature of the solution from 0° C. to 5° C. for 1 hour, then the mixture is stirred at 15° C. to 30° C. for 24 hours; the solvent is evaporated off to obtain 6-(nitrooxy)hexanoyl chloride in 88-97% w/w yield that is used without further purification.

Preparation of hexanoic acid, 6-(nitrooxy)-, (1S, 2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester (Compound (I))

All steps are carried out under nitrogen atmosphere.

Bimatoprost is added to methyltertbutyl ether, and the resulting solution is cooled to about 15° C. to 18° C.; successively n-butyl boronic acid (1.11-1.18 equivalents) is added in one portion and the mixture is stirred for about 1-1.5 hour at 40° C. The end of the reaction is monitored by $^1$H NMR analysis; the reaction mixture is cooled down to about 20° C. to 25° C., filtered and the formed water is removed by azeotropic distillation of methyltertbutyl ether at a temperature equal to or below 40° C., until water content is below or equal to 0.25%, to give crude bimatoprost boronate (compound (II)) which is used in the next step without further purification;

The crude bimatoprost boronate (compound (II)) is added to methyltertbutyl ether and the resulting solution is cooled to about 0° C. to 5° C., 4-dimethylaminopyridine (about 2.1-2.3 equivalent) is added, 6-(nitrooxy)hexanoyl chloride (IVa) (1.5 equivalents) dissolved in methyltertbutyl ether is dropwise added keeping the temperature of the mixture at about 0° C. to 5° C. After the addition, the mixture is stirred at about 0° C. to 5° C. up to 4 hours then overnight up to 15° C. to 20° C.; the end of the reaction is monitored by HPLC analysis; (1 S,2E)-3-{(6R,7R)-3-butyl-7[(2Z)-7-(ethylamino)-7-oxohept-2-en-1-yl]-2,4-dioxa-3-borabicyclo[3.2.1]oct-6-yl}-1-(2-phenylethyl)-prop-2-en-1-yl-6-(nitrooxy) hexanoate (compound (III)) is isolated by standard work-up methods (an example of work up is described in Example 1);

(1S,2E)-3-{(6R,7R)-3-butyl-7[(2Z)-7-(ethylamino)-7-oxohept-2-en-1-yl]-2,4-dioxa-3-borabicyclo[3.2.1]oct-6-yl}-1-(2-phenylethyl)-prop-2-en-1-yl-6-(nitrooxy) hexanoate (compound (III)) is dissolved in methanol and the resulting solution is stirred for about 18 hours at 17° C. to 25° C.; the conversion of compound (III) to compound (I) is monitored by $^1$H NMR. In case the reaction stops, the mixture is evaporated and re-dissolved in fresh methanol until complete conversion. The reaction mixture is then concentrated under vacuum at a temperature below 40° C. and the crude hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester (compound (I)) is isolated by standard methods of work up.

The HPLC quantitative analysis of the crude reaction mixture detects a content of compound (I) of about 70%, an amount of 15-(6-chlorohexanoyl) ester of bimatoprost (compound (X)) of about 0.12% and an amount of dimeric impurity (compound (XII)) below the HPLC detection limit of 0.05% (see Table 1).

The crude reaction mixture is purified by column chromatography using a silica gel column and a mixed solvent of dichloromethane and methanol to give compound (I) with an overall yield of above 60% w/w with respect to bimatoprost.

The HPLC quantitative analysis purity of compound (I) is above 98%, the amount of 15-(6-chlorohexanoyl) ester of bimatoprost (compound (X)) is less than 0.15% and the content of dimeric impurity (compound (XII)) is below 0.05%.

The process of the invention provides hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester (I)) in high yield and high purity and having a reducing amounts of by-products, in particular of the (S,E)-1-((1R,2R,3S,5R)-2-((Z)-7-(ethylamino)-7-oxohept-2-enyl)-3,5-dihydroxycyclopentyl)-5-phenylpent-1-en-3-yl 6-chlorohexanoate (compound (X)), which is predicted as positive for bacterial in vitro mutagenicity, and of the 6-{[6-(nitrooxy)hexanoyl]oxy}hexanoic acid ester of bimatoprost (compound (XII)).

The above advantages make the process of the invention a cost effective process easily transferable to the industrial scale.

EXPERIMENTAL EXAMPLES

All synthesis steps described below were conducted under nitrogen atmosphere.

Example 1

Synthesis of hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester (compound (I))

Synthesis of 6-(nitrooxy)hexanoyl chloride (Compound (IV))

Step 1: Synthesis of 6-hydroxyhexanoic acid potassium salt (Compound (VI))

A solution of potassium hydroxide (1.98 g, 1 equivalent) in methanol (10 ml) was prepared under cooling at 15° C. to 20° C. and was added at 5° C. to 20° C. within 0.5 hour to a solution of 3.65 g of 2-caprolactone (1 equivalent) in methanol (6 ml). The mixture was stirred for 4.5 hours at 15° C. to 20° C. The reaction mixture was concentrated under vacuum (at a temperature equal to or below 40° C.) to give crude 6-hydroxyhexanoic acid potassium salt (6.10 g). The crude was re-slurred in methyltertbutyl ether (10 ml) for 4 hours at 20° C. to 25° C., filtered, washed with methyltertbutyl ether (2×25 ml) and dried under vacuum at (temperature equal to or below 40° C.) to give 6-hydroxyhexanoic acid potassium salt (5.16 g) with 93.7% yield. Melting point 208° C.

Step 2: Synthesis of 6-(nitrooxy)hexanoic acid (Compound (VIIa))

Fuming $HNO_3$ (4.6 equivalents) was added to concentrated $H_2SO_4$ (3.1 equivalent) at a temperature from 0° C. to 5° C. in 14 min, then $CH_2Cl_2$ (20 ml) was added at a temperature from 0° C. to 5° C. in 12 min. 6-Hydroxyhexanoic acid potassium salt (10.13 g, 1 equivalent) was added portion-wise in 28 min at temperature below 10° C. The mixture stirred for 2.2 hours at 0° C. to 10° C. and the reaction was monitored by $^1$H-NMR showing 99.9% conversion. The mixture was cooled to 0° C. to 5° C. and saturated sodium chloride aqueous solution was added carefully at a temperature equal to or below 10° C. within 17 min. After filtration, the organic layer was decanted, dried over sodium sulfate and concentrated under vacuum (at a temperature equal to or below 40° C.) to give 9.15 g of 6-(nitrooxy)hexanoic acid (87.7% yield) with 96.2% HPLC purity and a content of 6-{[6-(nitrooxy)hexanoyl]oxy}hexanoic acid (compound (VIIb)) of 0.75%.

Step 3: Purification of Crude 6-(nitrooxy)hexanoic acid (Compound (VIIa)) Containing 6-{[6-(nitrooxy)hexanoyl]oxy}hexanoic acid (Compound (VIIb))

1.5 g of crude 6-(nitrooxy)hexanoic acid (VIIa), obtained in Step 2, were loaded on a Purezza®-Sphera$^{Plus}$ Flash Cartridges—C18, 25μ—Standard Type Flash Cartridge, 48 g, and eluted with $H_2O$+HCOOH 0.1%/Acetonitrile from 90:10 to 75:25. The fractions containing compound (VIIa), eluted at 78:22 were collected and then extracted with $CH_2Cl_2$ (3×150 mL), dried over sodium sulfate and concentrated under vacuum at a temperature below 40° C. to afford 6-(nitrooxy)hexanoic acid 1.04 g (69% yield) having HPLC purity >99.5% and an amount of compound (VIIb) <0.05%.

Step 4: Synthesis of 6-(nitrooxy)hexanoyl chloride (Compound (IVa))

6-(Nitrooxy)hexanoic acid (2.61 g, 1 equivalents) was dissolved in dichloromethane (15 ml) and cooled to 0° C. to 5° C. under nitrogen. Then N,N-dimethylformamide (0.16 ml) and oxalyl chloride (1.93 g) were added at 0° C. to 5° C. within 34 minutes. The reaction mixture was stirred at 0° C. to 5° C. for 3.5 hours and then for 14 hours at 15° C. to 20° C. Then the reaction mixture was concentrated under vacuum (temperature is equal to or below 40° C.) and co-evaporated with dichloromethane to give 6-(nitrooxy)hexanoyl chloride (compound (IVa)) (2.8 g) with 97% yield.

Step 5: Synthesis of (Z)-7-[(1S,5R,6R,7R)-3-butyl-6-[((E,3S)-3-hydroxy-5-phenyl-pent-1-enyl]-2,4-dioxa-3-borabicyclo[3.2.1)octan-7-yl]-N-ethyl-hept-5-enamide (Compound (II))

Bimatoprost (2.3 g, 1 equivalent) was dissolved in Methyltertbutyl ether (30 ml) and Butyl boronic acid (0.62 g, 1.13 equivalents) was added. The mixture was heated to 40° C. for 1 hour. The reaction was monitored by $^1$H NMR till conversion >97%.

The reaction mixture was rinsed with methyltertbutyl ether (10 ml) and the mixture was heated at a temperature about 40° C. under vacuum for azeotropic distillation. Rinsing with methyltertbutyl ether and azeotropic distillation were continued till the water content of (Z)-7-[(1S,5R,6R,7R)-3-butyl-6-[((E,3S)-3-hydroxy-5-phenyl-pent-1-enyl]-2,4-dioxa-3-borabicyclo[3.2.1)octan-7-yl]-N-ethyl-hept-5-enamide (compound (II)) was equal to or below 0.25%. Compound (II) was obtained with quantitative yield (2.84 g).

Step 6: Synthesis of (1S,2E)-3-{(6R,7R)-3-butyl-7[(2Z)-7-(ethylamino)-7-oxohept-2-en-1-yl]-2,4-dioxa-3-borabicyclo[3.2.1]oct-6-yl}-1-(2-phenylethyl)-prop-2-en-1-yl 6-(nitrooxy) hexanoate (Compound (III))

(Z)-7-[(1S,5R,6R,7R)-3-Butyl-6-[((E,3S)-3-hydroxy-5-phenyl-pent-1-enyl]-2,4-dioxa-3-borabicyclo[3.2.1)octan-7-yl]-N-ethyl-hept-5-enamide (compound (II)) (3.21 g, 1 equivalent) was dissolved in Methyltertbutyl ether (30 ml) under and cooled to 0° C. to 5° C. 4-Dimethylaminopyridine (1.85 g, 2.27 equivalents) was added in one portion. A solution of 6-(nitrooxy)hexanoyl chloride (compound (IVa)) (1.96, 1.5 equivalents) in methyltertbutyl ether (5 ml), was added dropwise at 0° C. to 5° C. within 1 hour. After stirring for 24 minutes at 0° C. to 5° C., and at 15° to 20° C. for 14.5 hours, the reaction mixture was cooled at 0° C. to 5° C. and deionized water was added within 20 minutes at a maximum temperature of 15° C.

The mixture was stirred for 5 minutes. The aqueous layer was discarded. The organic layer was washed with the 1N hydrochloric acid solution then with deionized water and last with brine.

The organic layer was dried over sodium sulfate and concentrated under vacuum to afford (1S,2E)-3-{(6R,7R)-3-butyl-7 [(2Z)-7-(ethylamino)-7-oxohept-2-en-1-yl]-2,4-dioxa-3-borabicyclo[3.2.1]oct-6-yl}-1-(2-phenylethyl)-prop-2-en-1-yl 6-(nitrooxy) hexanoate (compound (III)) (4.1 g, 94% yield)

Step 7: Synthesis of hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester (I) (Compound (I))

(1S,2E)-3-{(6R,7R)-3-butyl-7[(2Z)-7-(ethylamino)-7-oxohept-2-en-1-yl]-2,4-dioxa-3-borabicyclo[3.2.1]oct-6-yl}-1-(2-phenylethyl)-prop-2-en-1-yl 6-(nitrooxy) hexanoate (compound (III)) (4 g crude, 1 equivalent) was dissolved in methanol (30 ml) and the resulting solution was stirred at room temperature for 24 hours monitoring the reaction by $^1$H-NMR. Then methanol was removed under vacuum at 35° C. to 40° C. The residue was dissolved in methyltertbutyl ether and washed with deionized water and then brine. The organic layer was dried over sodium sulfate and concentrated under vacuum at a temperature below 40° C. to afford crude reaction mixture (3.8 g) that, after HPLC (% area) reverse phase quantitative analysis showed that the amount of compound (I) in the mixture was 73%, the content of 15-(6-chlorohexanoyl) ester of bimatoprost (compound (X)) was 0.11% and the content of the dimeric impurity 6-{[6-(nitrooxy)hexanoyl]oxy}hexanoic acid ester of bimatoprost (compound (XII)) was below 0.05% (see Table 1).

The residue was chromatographed on silica gel column with dichloromethane/methanol 95:5 as eluent. The fractions were monitored by TLC and only pure fractions were mixed and concentrated under vacuum at a temperature equal to or below to 40° C. yielding compound (I) with a HPLC purity >98%, the content of 15-(6-chlorohexanoyl) ester of bimatoprost (compound (X)) was 0.11% and the content of the dimeric impurity 6-{[6-(nitrooxy)hexanoyl]oxy}hexanoic acid ester of bimatoprost (compound (XII)) was below 0.05%

Example 2 (Comparative Example)

Synthesis of hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester (Compound (I)) According to the Procedure Disclosed in WO 2009/136281 (Scheme 3 Below)

Step A: Preparation of (Z)-7-[(1S,5R,6R,7R)-3-butyl-6-[((E,3S)-3-hydroxy-5-phenyl-pent-1-enyl]-2,4-dioxa-3-borabicyclo[3.2.1)octan-7-yl]-N-ethyl-hept-5-enamide (Compound (II))

Butylboronic acid (1.129 equivalents) was added to a solution of bimatoprost (1 g, 1 equivalent) in dichloromethane (16 ml) The mixture was heated to 40° C. for 1 hour, monitoring the progression of the reaction by $^1$H-NMR. Solvent was removed under reduced pressure for 2 hours. Dichloromethane (16 ml) was added and the mixture was heated to 40° C. for another hour. Solvent was removed under pressure for 40 min. Dichloromethane (16 ml) was added and the mixture was heated to 40° C. for 16 hours. Solvent was evaporated and the crude product was dried under high vacuum at 40° C. for 3 hours, yielding compound (II) in quantitative yield that was used in the next step without any further purification.

MS: m/z=438 [M+H]+

Step B: Synthesis of (S,E)-1-((1S,5R,6R,7S)-3-butyl-7-((Z)-7-(ethylamino)-7-oxohept-2-en-1-yl)-2,4-dioxa-3-borabicyclo[3.2.1]octan-6-yl)-5-phenylpent-1-en-3-yl 6-bromo hexanoate (Compound (XI)

4-Dimethylaminopyridine (1.1 eq.) and 6-bromohexanoyl chloride (1.15 equivalent) were added to a solution of compound (II) (0.8 g, 1 equivalent) in dichloromethane (15.3 ml) cooled to 0-5° C. The mixture was stirred for 0.5 hour at 0° C. to 5° C. and 16 hours at 20° C. to 25° C.

4-Dimethylaminopyridine (0.25 equivalent) and 6-bromohexanoyl chloride (0.25 equivalent) were added and the mixture was stirred for 19 additional hours. The reaction was monitored by $^1$H-NMR till complete conversion. The mixture was diluted with dichloromethane (15.3 ml) and the organic solution was washed with deionized water (6.25 ml) and brine (6.25 ml). The organic phase was dried over $Na_2SO_4$ and concentrated under vacuum, to give compound (XI) as a light yellow oil, (calculated as quantitative yield) used in the next step without further purification.

Step C: Synthesis of hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester (Compound (I))

Silver nitrate (3.72 equivalent) was added to a solution of compound (VIII) (0.8 g, 1 equivalent) in acetonitrile (9.4 ml). The mixture was stirred for 18 hours at 20° C. to 25° C. The conversion was monitored by $^1$H-NMR in DMSO.

Silver nitrate (0.5 eq.) was added and the mixture was stirred for 20 additional hours until HPLC analysis showed 99.7% conversion.

The mixture was filtered on a Whatman filter. The filtrate was concentrated under vacuum. The residue was dissolved in ethyl acetate (30 ml). The organic phase was washed with deionized water (5 ml) and brine (5 ml). After drying over $Na_2SO_4$, the layer was concentrated under vacuum. The residue was chromatographed on silica gel column with dichloromethane/methanol 95:5 as eluent. The fractions were monitored by TLC, pure fractions were mixed and concentrated under vacuum at a temperature equal to or below to 40° C. yielding compound (I) in 86% overall yield along with 4.27% of bimatoprost.

HPLC (% area) reverse phase quantitative analysis showed that purity of compound (I) after chromatography was 77% and the content of 15-(6-chlorohexanoyl) ester of bimatoprost (compound (X)) is 8.34%.

TABLE 1

| HPLC quantitative analysis | | | | |
|---|---|---|---|---|
| | Content (%) | | | |
| Example | Compound (I) (%) | Impurity (XII) % | Impurity (X) % | Bimatoprost % |
| 1 | 73[#] | <0.05% | 0.11 | 0 |
| 2 | 77* | n.a | 8.34 | 4.27 |

[#]Amount of compound (I) in the crude reaction mixture of Step 7 of Example 1

*The compound was chromatographed on silica gel at the end of Step C

Table 1 reports the results of the HPLC quantitative analysis of compound (I) and of the main impurities formed during the preparation of compound (I) according to the processes of the invention (Example 1) and to a method discloses in WO 2009/136281 (Example 2).

Compound (X) is the 15-(6-chlorohexanoyl) ester of bimatoprost that is predicted as positive for bacterial in vitro mutagenicity. The results show that the processes of the invention provides compound (I) with a content of compound (X) of 0.11% and a content of the "dimer impurity" 6-{[6-(nitrooxy)hexanoyl]oxy}hexanoic acid ester of bimatoprost (compound (XII)) below the detection limit of 0.05%. The process disclosed in the prior art leads to compound (I) having a lower chemical purity and a content of compound (X) of 8.34%, namely more than 30 fold higher than the amount of compound (X) formed in the process of the invention.

The results demonstrate that the process of the invention represents an improvement over the method described in the prior art.

SCHEME 3
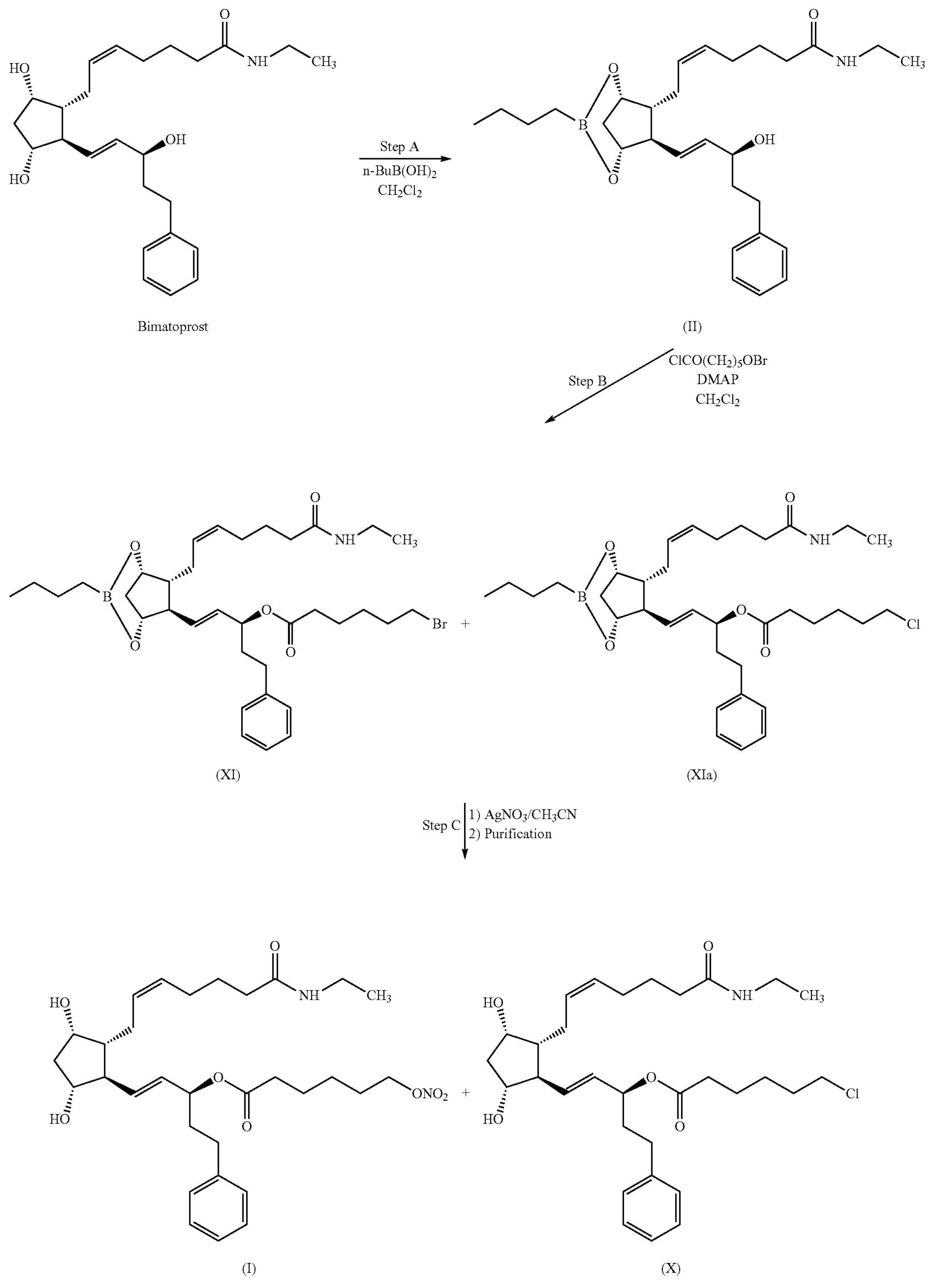
Bimatoprost
(II)
(XI)
(XIa)
(I)
(X)

The invention claimed is:

1. A process for the preparation of hexanoic acid, 6-(nitrooxy)-(1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester of formula (I):

(I)

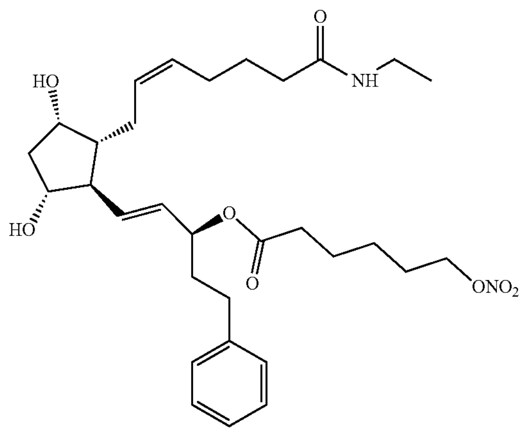

said process comprising the following steps:

1) reacting a compound of formula (II):

(II)

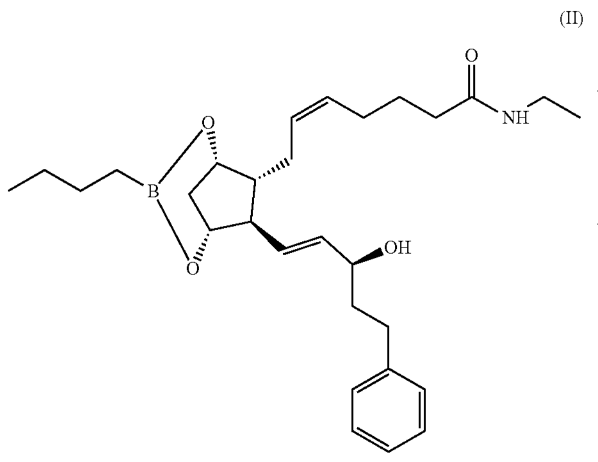

with a 6-(nitrooxy)hexanoyl chloride of formula (IVa)

(IVa)

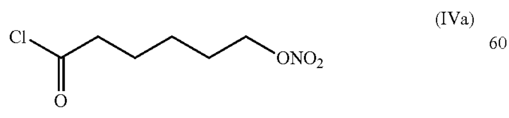

in the presence of 4-dimethylaminopyridine in free form, to obtain a compound of formula (III) having a boronate protective group (III)

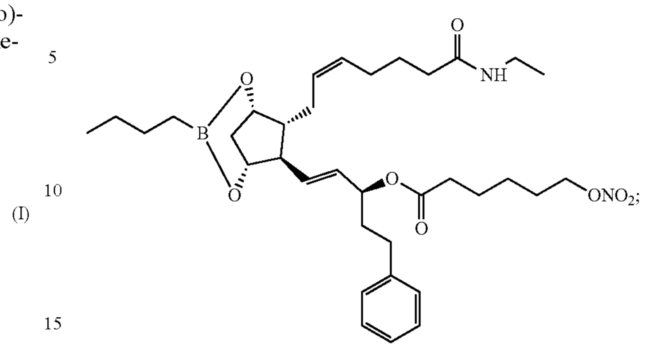

2) removing the boronate protective group of the compound of formula (III) to obtain a compound of formula (I); and 3) purifying the compound of formula (I);

wherein the 6-(nitrooxy)hexanoyl chloride (IVa) of step 1) is prepared by a process comprising:

4) reacting a 2-caprolactone of formula (V)

(V)

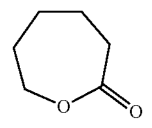

with an inorganic base selected from KOH, NaOH and LiOH to obtain a 6-hydroxyhexanoic acid salt of formula (VI)

(VI)

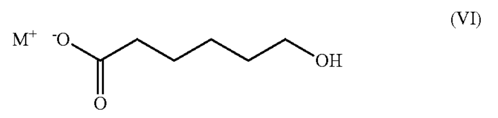

wherein M is K, Na or Li;

5) nitrating a compound of formula (VI) with a mixture of $HNO_3$ and $H_2SO_4$ to obtain a 6-(nitrooxy)hexanoic acid of formula (VIIa);

(VIIa)

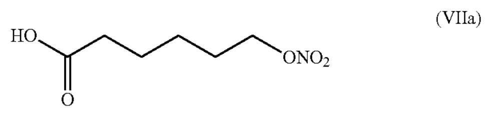

6) purifying the 6-(nitrooxy)hexanoic acid of formula (VIIa) to provide a pure 6-(nitrooxy)hexanoic acid of formula (VIIa) by reverse phase chromatography using formic acid in water ($H_2O$+HCOOH) and acetonitrile as eluent to obtain a plurality of chromatographic fractions, wherein the pure 6-(nitrooxy)hexanoic acid of formula (VIIa) has a content of 6-{[6-(nitrooxy)hexanoyl]oxy}hexanoic acid (a compound of formula (VIIb))

(VIIb)

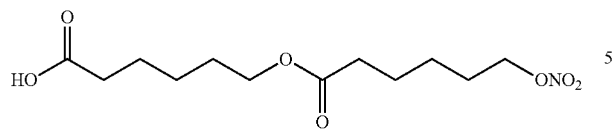

below an HPLC detection limit of 0.05%; and 7) reacting the pure 6-(nitrooxy)hexanoic acid of formula (VIIa) with a chlorinating agent to obtain the 6-(nitrooxy)hexanoyl chloride (IVa).

2. The process according to claim 1 wherein step 1) is carried out at a temperature ranging from 0° C. to room temperature in an aprotic organic solvent.

3. The process according to claim 2 wherein the aprotic organic solvent is methyltertbutyl ether.

4. The process according to claim 1 wherein in step 1) the molar ratio of compound (II) to 6-(nitrooxy) hexanoyl chloride (IVa) is from 1:1.4 to 1:1.6 and the molar ratio of compound (II) to 4-dimethylaminopyridine is from 1:2.0 to 1:2.4.

5. The process according to claim 1 wherein in step 4) the inorganic base is potassium hydroxide.

6. The process according to claim 1 wherein step 4) is carried out in a solvent selected from methanol, ethanol or isopropanol.

7. The process according to claim 6 wherein the solvent is methanol.

8. The process according to claim 1 wherein step 5) is carried out in dichloromethane.

9. The process according to claim 1 wherein in step 6) the concentration of the formic acid in water ($H_2O$+HCOOH) is 0.1% w/w.

10. The process according to claim 1 wherein in step 6), one or more chromatographic fractions of the plurality of chromatographic fractions are extracted with a solvent comprising $CH_2Cl_2$, dried and the solvent is evaporated, the one or more one or more chromatographic fractions containing the compound of formula (VIIa).

11. The process according to claim 1 wherein step 7) is carried out in dichloromethane and the chlorinating agent is oxalyl chloride.

12. A process for the preparation of hexanoic acid, 6-(nitrooxy) (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester of formula (I);

(I)

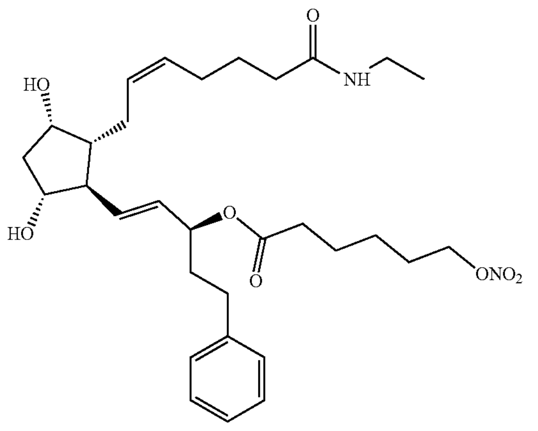

comprising:

reacting a 2-caprolactone of formula (V)

(V)

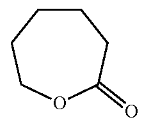

with an inorganic base selected from KOH, NaOH and LiOH to obtain a 6-hydroxyhexanoic acid salt of formula (VI)

(VI)

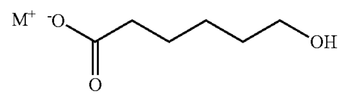

wherein M is K, Na or Li;

nitrating the 6-hydroxyhexanoic acid salt of formula (VI) with a mixture of $HNO_3$ and $H_2SO_4$ to obtain a 6-(nitrooxy) hexanoic acid of formula (VIIa)

(VIIa)

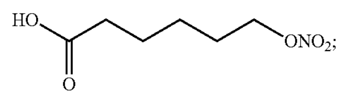

purifying the 6-(nitrooxy) hexanoic acid of formula (VIIa) to provide a pure 6-(nitrooxy) hexanoic acid of formula (VIIa) by reverse phase chromatography using formic acid in water ($H_2O$+HCOOH) and acetonitrile as eluent to obtain a plurality of chromatographic fractions, wherein the pure 6-(nitrooxy) hexanoic acid of formula (VIIa) has a content of 6-{[6-(nitrooxy) hexanoyl]oxy}hexanoic acid (a compound of formula (VIIb))

(VIIb)

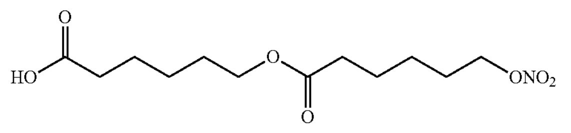

below an HPLC detection limit of 0.05%;

reacting the pure 6-(nitrooxy) hexanoic acid of formula (VIIa) with a chlorinating agent to obtain a 6-(nitrooxy) hexanoyl chloride of formula (IVa)

(IVa)

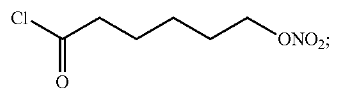

without purification of the 6-(nitrooxy) hexanoyl chloride of formula (IVa), reacting the 6-(nitrooxy) hexanoyl chloride of formula (IVa) with a compound of formula (II);

(II)

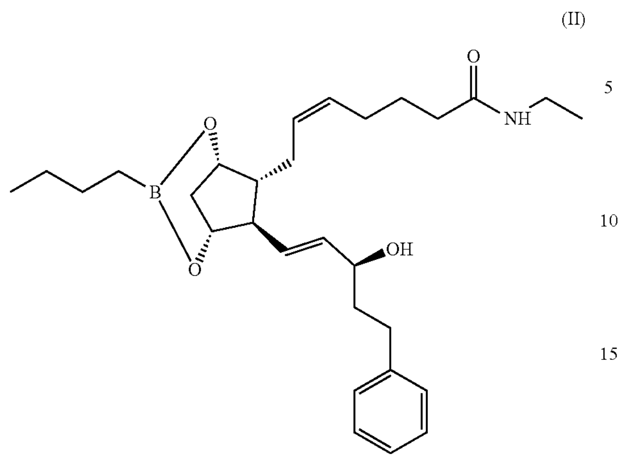

in the presence of 4-dimethylaminopyridine in free form, to obtain a compound of formula (III) having a boronate protective group (III)

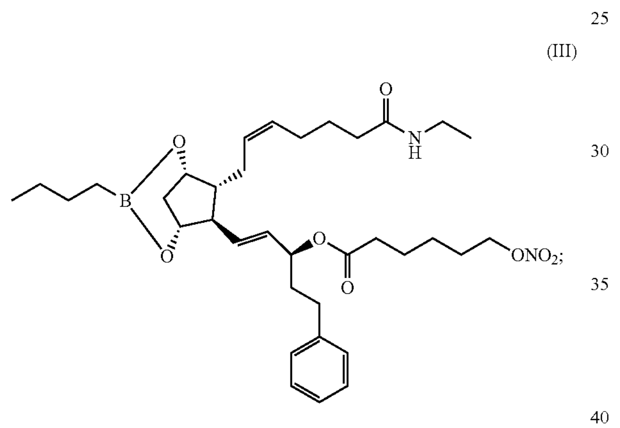

and removing the boronate protective group of the compound of formula (III) to obtain a compound of formula (I); and purifying the compound of formula (I).

13. A process for the preparation of 6-(nitrooxy) hexanoic acid (compound (VIIa)) having a purity of 99% and a content of {[6-(nitrooxy) hexanoyl]oxy}hexanoic acid (compound (VIIb)) less than 0.05%, wherein said process comprises the following steps:

4) Reacting 2-caprolactone (V)

(V)

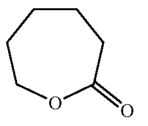

with KOH in methanol to obtain 6-hydroxyhexanoic acid salt of formula (VI)

(VI)

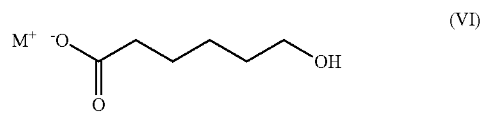

wherein M is K;

5) Nitrating the compound of formula (VI) with a mixture of $HNO_3$ and $H_2SO_4$ in dichloromethane at a temperature from about 5° C. to 10° C.;

6) Purifying the mixture by reverse phase chromatography using a solution of 0.1% formic acid in water and acetonitrile as eluents, followed by extraction of fractions with dichloromethane to obtain the 6-(nitrooxy) hexanoic acid (VIIa)

(VIIa)

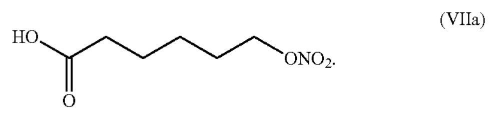

14. The process of claim 13, wherein nitrating the compound of formula (VI) with the mixture of $HNO_3$ and $H_2SO_4$ in dichloromethane is performed at a temperature of 10° C.

15. Hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester of formula (I) having a chemical purity above 98% and containing an amount of 15-(6-chlorohexanoyl) ester of bimatoprost (compound (X)) of about 0.12%

(X)

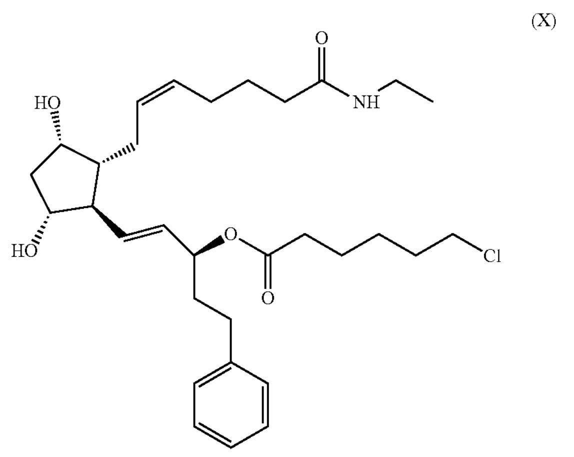 [SMILES: CCNC(=O)CCC/C=C\C[C@@H]1[C@@H](/C=C/[C@H](CCc2ccccc2)OC(=O)CCCCCCl)[C@H](O)C[C@@H]1O]

and an amount of 6-{[6-(nitrooxy) hexanoyl]oxy}hexanoic acid ester of bimatoprost (compound (XII)) below 0.05%

(XII)

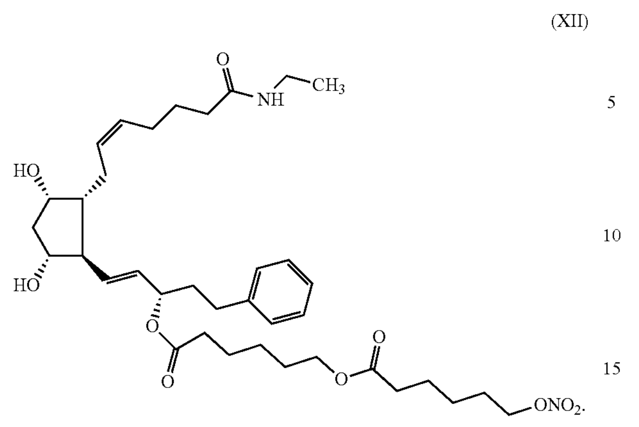

16. A pharmaceutical formulation containing hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester of formula (I) and at least a pharmaceutically acceptable excipient, wherein hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester has a chemical purity above 98%, and contains an amount of 15-(6-chlorohexanoyl) ester of bimatoprost (compound (X)) about 0.12% and an amount of the dimeric impurity 6-{[6-(nitrooxy) hexanoyl]oxy}hexanoic acid ester of bimatoprost (compound (XII)) below 0.05%.

* * * * *